United States Patent
Hasegawa

(10) Patent No.: US 10,492,874 B2
(45) Date of Patent: Dec. 3, 2019

(54) MEDICAL SYSTEM AND METHOD OF OPERATION THEREOF

(71) Applicant: Olympus Corporation, Hachioji-shi, Tokyo (JP)

(72) Inventor: Mitsuaki Hasegawa, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 16/171,467

(22) Filed: Oct. 26, 2018

(65) Prior Publication Data
US 2019/0060009 A1 Feb. 28, 2019

Related U.S. Application Data

(63) Continuation of application No. PCT/JP2016/086311, filed on Dec. 7, 2016.

(51) Int. Cl.
*G06F 19/00* (2018.01)
*A61B 34/30* (2016.01)
(Continued)

(52) U.S. Cl.
CPC ............ *A61B 34/30* (2016.02); *B25J 9/0084* (2013.01); *B25J 11/008* (2013.01); *B25J 13/06* (2013.01);
(Continued)

(58) Field of Classification Search
CPC . A61B 34/30; A61B 1/00045; A61B 1/00149; A61B 2034/302; A61B 34/37;
(Continued)

(56) References Cited

U.S. PATENT DOCUMENTS 9,468,501 B2 * 10/2016 Hourtash .............. B25J 9/1607
9,510,911 B2 * 12/2016 Hourtash .............. A61B 34/37
(Continued)

FOREIGN PATENT DOCUMENTS

| JP | 2010-240793 | 10/2010 |
| JP | 2011-206312 | 10/2011 |

(Continued)

OTHER PUBLICATIONS

International Search Report and Written Opinion from corresponding International Application No. PCT/JP2016/086311, dated Mar. 7, 2017.

*Primary Examiner* — Ian Jen
(74) *Attorney, Agent, or Firm* — Matthew M. Eslami

(57) ABSTRACT

A medical system includes a plurality of arms including a joint group having a redundant degree of freedom. The plurality of arms is configured to move medical devices mounted on their free end. An operation portion is configured to input an operation command for operating the plurality of arms. A controller controls the plurality of arms based on the operation command from the operation portion. The controller includes one or more processor as a hardware. The processor configured to predict an interference between the plurality of arms, calculate degrees of priority of each of the plurality of arms based on severities of effects by the predicted interference on a patient, and operate a signal of the plurality of arms having highest degrees of priority. The signal is configured so that the plurality of arms can avoid the interference.

6 Claims, 3 Drawing Sheets

(51) Int. Cl.
*B25J 11/00* (2006.01)
*B25J 13/06* (2006.01)
*B25J 9/00* (2006.01)
*A61B 1/00* (2006.01)

(52) U.S. Cl.
CPC ....... *A61B 1/00045* (2013.01); *A61B 1/00149* (2013.01)

(58) Field of Classification Search
CPC ... A61B 2090/065; B25J 9/0084; B25J 13/06; B25J 11/008; B25J 9/1666
See application file for complete search history.

(56) References Cited

U.S. PATENT DOCUMENTS

| | | | | |
|---|---|---|---|---|
| 2011/0245844 | A1* | 10/2011 | Jinno | A61B 34/71 606/130 |
| 2013/0041219 | A1* | 2/2013 | Hasegawa | B25J 13/02 600/109 |
| 2013/0325031 | A1* | 12/2013 | Schena | A61B 34/37 606/130 |
| 2014/0276952 | A1* | 9/2014 | Hourtash | B25J 9/1638 606/130 |
| 2014/0277741 | A1* | 9/2014 | Kwon | B25J 9/1689 700/263 |
| 2014/0316430 | A1* | 10/2014 | Hourtash | B25J 9/1607 606/130 |
| 2016/0278871 | A1 | 9/2016 | Schena et al. | |
| 2017/0035518 | A1 | 2/2017 | Hourtash et al. | |
| 2019/0060009 | A1* | 2/2019 | Hasegawa | A61B 34/30 |

FOREIGN PATENT DOCUMENTS

| | | |
|---|---|---|
| JP | 2014-180751 | 9/2014 |
| JP | 2016-516487 | 6/2016 |
| WO | 2013018908 | 2/2013 |
| WO | 2014146107 | 9/2014 |

* cited by examiner

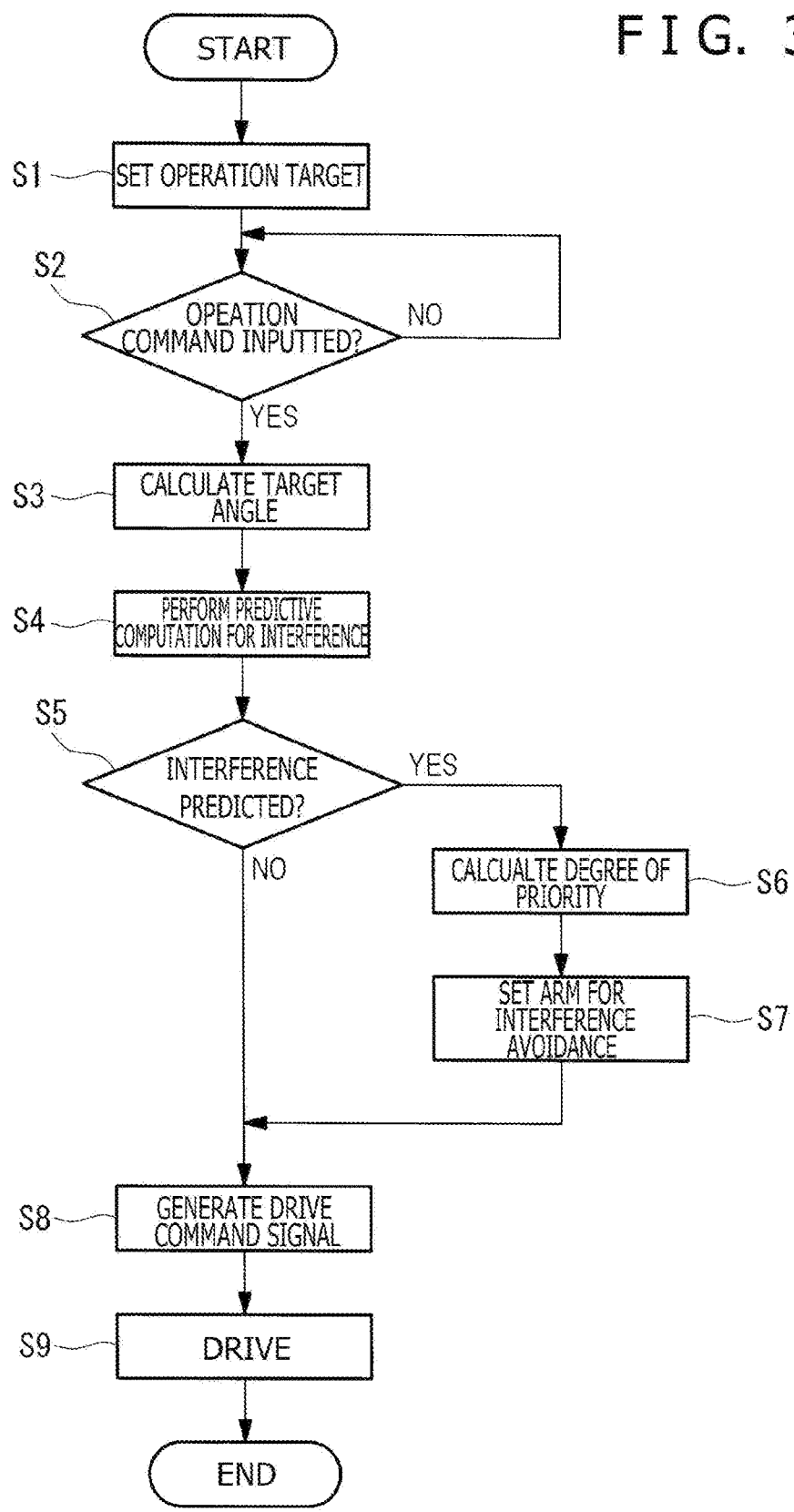

MEDICAL SYSTEM AND METHOD OF OPERATION THEREOF

CROSS-REFERENCE TO RELATED APPLICATION(S)

This application is a continuation application of PCT Application No. PCT/JP 2016/086311 filed on Dec. 7, 2016, which is hereby incorporated by reference in its entirety.

TECHNICAL FIELD

The disclosed technology relates to a medical system and a method of operation thereof.

DESCRIPTION OF THE RELATED ART

Medical systems with a plurality of arms each of which has joints with redundant degrees of freedom are generally known. For example, U.S. Patent Application Publication No. 20130325031 (hereinafter, U.S. Pub. '031) discloses a minimally invasive robotic surgery system using the redundancy of joints that form each arm. These medical systems move the position of each joint of the arm without changing the orientation of an associated surgical instrument, whereby an interference between arms or an interference between an arm and an obstacle is avoided. However, in U.S. Pub. '031 there is a need to perform enormous calculations at high speed which requires to use a high-performance computer so that each arm is allowed to automatically perform an interference avoidance maneuver. Particularly, to avoid an interference while allowing the surgical instrument to move in real time by an operation of a master console, a still greater number of calculations needs to be performed in real time, causing the inconveniences of high manufacturing cost and unstable operation.

BRIEF SUMMARY OF EMBODIMENTS

One aspect of the technology disclosed herein is directed to a medical system having a plurality of arms each of which comprising a joint group having a redundant degree of freedom. The plurality of arms is configured to move medical devices mounted on their free end. An operation portion is configured to input an operation command for operating at least one of the plurality of arms. A controller is configured to control the at least one of the plurality of arms based on the operation command from the operation portion. The controller includes one or more processor as a hardware. The one or more processors configured to (i) predict an interference between the plurality of arms, (ii) calculate degrees of priority of each of the plurality of arms based on severities of effects by the predicted interference on a patient, and (iii) operate a signal of one of the plurality of arms having highest one of the degrees of priority. The signal is configured so that the one of the plurality of arms can avoid the interference.

Another aspect of the technology disclosed herein is directed to a method of operation for a medical system. The method comprises the step of predicting an interference between plurality of arms. Next, calculating degrees of priority of each of the plurality of arms based on severities of effects by the predicted interference on a patient. Finally, generating a signal of one of the plurality of arms having highest one of the degrees of priority and the signal is configured such that the one of the plurality of arms can avoid the interference.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 3 is a flow chart illustrating a method of operation of the medical system of FIG. 1.

DETAILED DESCRIPTION OF THE EMBODIMENTS

Figure 1:
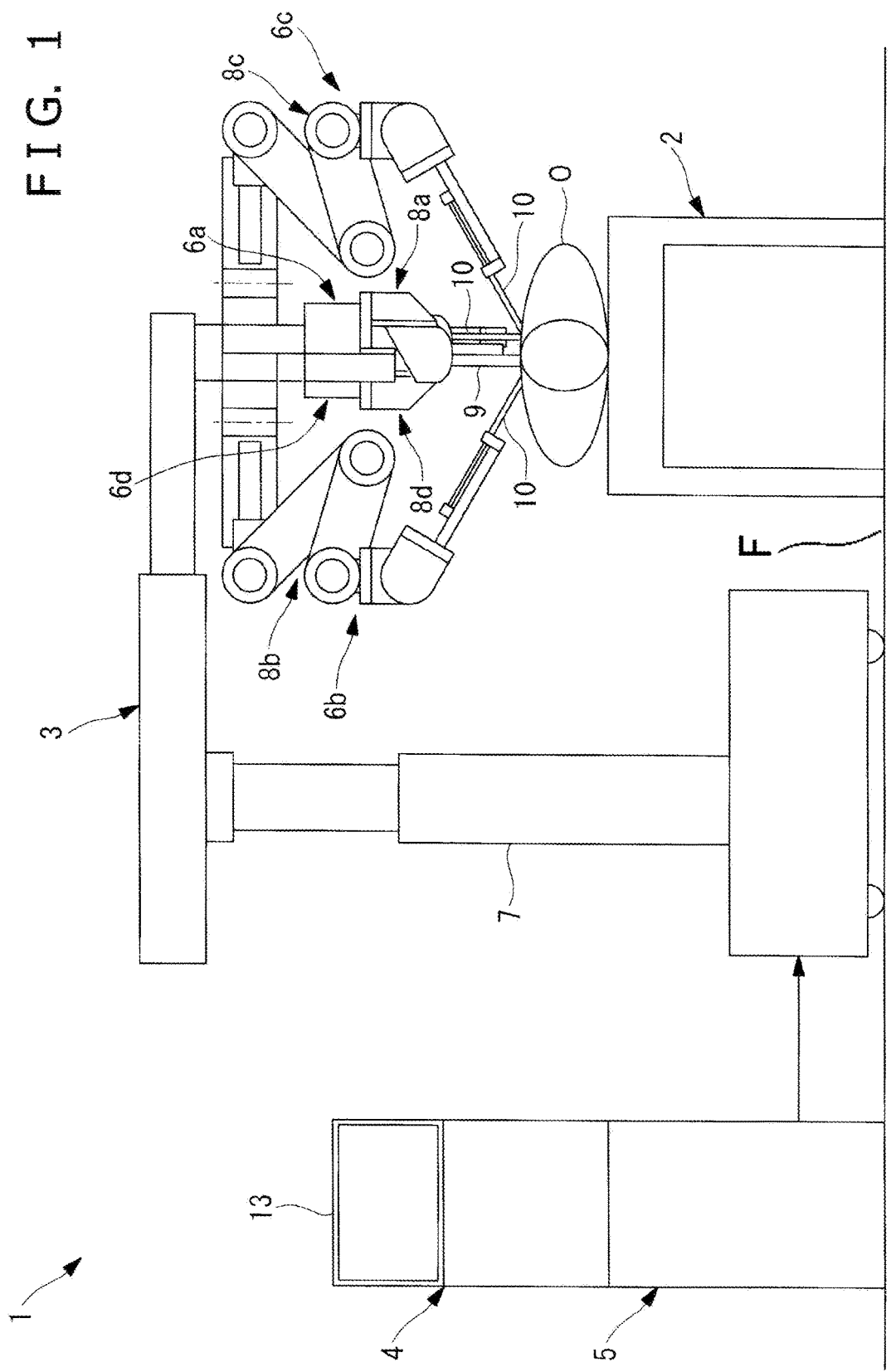
FIG. 1 is front view of a medical system according to an embodiment described herein.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Embodiments of the technology disclosed herein is directed to the provision of a medical system, which can avoid an interference of an arm while reducing the load of computation. A method of operation for this medical system is disclosed as well.

In one aspect of the present embodiment, a medical system includes a plurality of arms, an operation portion, and a controller. Each of the plurality of arms includes a joint group having a redundant degree of freedom. The plurality of arms is configured to move a medical device mounted on a free end thereof. The operation portion inputs an operation command for operating at least one of the arms. The controller controls the at least one arm based on the operation command inputted from the operation portion. The controller includes an interference prediction unit and a degree-of-priority calculating unit. The interference prediction unit predicts any interference of the at least one arm. The degree-of-priority calculating unit calculates degrees of priority of the plurality of arms based on severities of effects thereof on a subject or patient if an interference is predicted to occur by the interference prediction unit. The medical system moves one of the plurality of arms, the one arm having highest one of the degrees of priority calculated by the degree-of-priority calculating unit, in a direction away from the remaining arms. The controller may be formed by one or more processors as a hardware. The one or more processors may be constructed as programmable device such as CPUs, FPGAs, or the like, or devices such as ASICs.

According to this aspect, when an operator or a user operates the operation portion to input an operation command, the controller controls the at least one arm based on the inputted operation command, whereby treatment can be applied to a treatment target by the medical device. Here, with respect to the joints having redundant degrees of freedom, by keeping them inoperable, the controller can dispose, without performing enormous computation, the associated medical device at an appropriate position and in an appropriate orientation by determining operation angles of the individual joints.

While the at least one arm is operated by operating the operation portion, any interference between the plurality arms is predicted by the interference prediction unit provided in the controller. If an interference is predicted to occur by the interference prediction unit, the degrees of priority of the plurality of arms are calculated by the degree-of-priority calculating unit, and the arm having the highest degree of priority is moved in a direction away from the remaining arms.

Here, the degrees of priority of the plurality arms are calculated based on the severities of effects of the associated medical devices on the patient, and therefore the smaller the effect on the patient, the higher the degree of priority is set. Therefore, by moving the arm of the highest degree of priority in the direction away from the other arms, it is not necessary for each arm, the associated medical device of which gives a severer effect on the patient, to perform a calculation in real time for allowing to perform an interference avoidance maneuver in addition to the calculation for allowing to perform a maneuver by an operation command from the operation portion. Therefore, even if the operation becomes unstable due to the enormous calculations, effects on the patient are small so that interferences between arms can be avoided more definitely.

In the aspect described hereinbefore, the degree-of-priority calculating unit may calculate the degrees of priority based on types of the medical devices mounted on the arms. configured as described herein, it is possible to set the degree of priority low for each arm on which a medical device of a type having a great effect on the patient is mounted, and to set the degree of priority high for each arm on which a medical device of a type having a small effect on the patient is mounted. The degree-of-priority calculating unit also calculates the degrees of priority based on the operation states of the medical devices mounted on the arms. Even in the case of the same medical device, it is possible to set the degree of priority of the associated arm low if its effect on the patient is great that corresponds with the state of operation, and to operate the arm on which a medical device with a small effect on the patient is mounted.

The medical system further includes external force detection sensors that detect external forces applied to the medical devices, and the degree-of-priority calculating unit calculates the degrees of priority in proportion to magnitudes of the external forces detected by the external force detection sensors. If the external force detected by one of the external force detection sensors is large, there is a high possibility that the associated medical device is in contact with the patient under the large external force so that an operation of the associated arm would cause a great effect on the patient. By setting a degree of priority low for the arm, it is therefore possible to operate another arm with a medical device, which has a small effect on the patient. The controller operates one of the plurality of arms, the one arm having the highest one of the degrees of priority calculated by the degree-of-priority calculating unit, in a direction away from the remaining arms by operating at least one joint in the joint group of the one arm, the joint group having the redundant degree of freedom. The one arm can be operated without changing the orientation and position of the medical device mounted on the free end of the one arm. As a consequence, it is possible to avoid an interference between any two of the arms themselves without changing the orientations and positions of the medical devices relative to the treatment target.

In another aspect of the present embodiment, there is disclosed a method of operation of a medical system including a prediction step, a degree-of-priority calculating step and an interference avoidance maneuver step. The prediction step predicts any interference of at least one of a plurality of arms configured to move a medical device mounted on a free end thereof. Each of the plurality of arms includes a joint group having a redundant degree of freedom. The degree-of-priority calculating step calculates degrees of priority of the plurality of arms based on severities of effects thereof on a patient if an interference is predicted to occur in the prediction step. The interference avoidance maneuver step operates one of the plurality of arms, the one arm having highest one of the degrees of priority calculated in the degree-of-priority calculating step, in a direction away from the remaining arms. Therefore, the technology disclosed herein can bring about advantageous effects that an interference of an arm can be more effectively avoided while reducing the load of computation.

As depicted in FIG. 1, the medical system 1 according to this embodiment includes a bed 2 on which a subject, for example, a patient (O) is positioned. A surgical robot 3 arranged beside the bed 2, an operation portion 4 to be operated by an operator, and a controller 5 all of which are provided to perform an operation on the patient (O).

The surgical robot 3 includes a plurality of four arms 6a, 6b, 6c, and 6d and a mounting base 7 on which the respective arms 6a, 6b, 6c and 6d are supported. In FIG. 1, the arm 6a is positioned on the front side, while the arm 6d is positioned on the rear side. In the example depicted in FIG. 1, the mounting base 7 has an upstanding structure from a floor (F) beside the bed 2, but is not limited to such a structure and may be of a structure that is attached on a ceiling of a room. The arms 6a, 6b, 6c, and 6d include joint groups 8a, 8b, 8c, and 8d, respectively, and these joint groups 8a, 8b, 8c, and 8d each have a redundant degree of freedom with seven or more axes. A first medical device such as an endoscope or the like 9 is mounted on a free end of the first arm 6a, and second medical devices such as surgical instruments 10 are mounted on free ends of the remaining each of three arms (the second arm to the fourth arm) 6b, 6c, and 6d.

Figure 2:
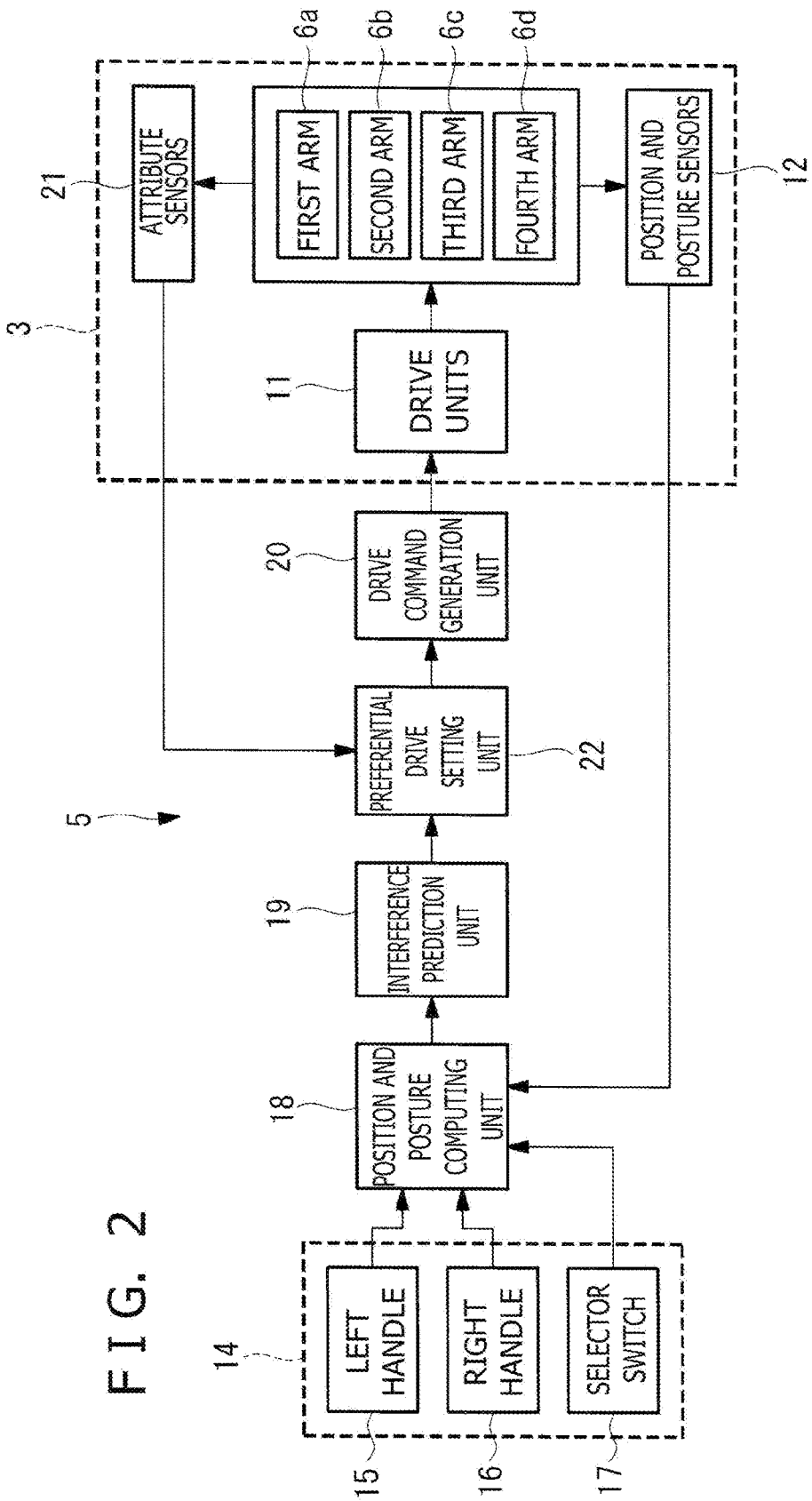
FIG. 2 is a block diagram depicting the medical system of FIG. 1.

As depicted in FIG. 2, the respective arms 6a, 6b, 6c, and 6d include respective drive units 11, position and orientation sensors 12, and attribute sensors 21. The drive units 11 such as electric motor or the like operate individual joints forming the arms 6a, 6b, 6c, and 6d. The position and orientation sensors 12 detect angles of the individual joints operated by the drive units 11. The attribute sensors 21, or external force sensors, detect the attributes of the endoscope 9 and the surgical instrument 10 mounted on the respective arms 6a, 6b, 6c, and 6d. The position and orientation sensors 12 are configured to detect the angles of the individual joints forming the respective arms 6a, 6b, 6c and 6d and the data is electronically communicated to a position and orientation computing unit 18. The attribute sensors 21 may be, for example, force sensors and/or sensors that detect whether the respective first and second medical devices 9 and 10 are in operation. The attribute sensors 21 detect external forces or the like acting on free end portions of the respective first and second medical devices 9 and 10, such as strain gauges attached to the free end portions of the medical devices 9 and 10. The attribute sensors 21 may output information on the endoscope 9 and surgical instruments 10. The attribute sensors 21 may output information on the type of medical device.

As depicted in FIG. 1 and FIG. 2, the operation portion 4 includes an operation input unit 14 to be operated by the user or operator, and a monitor 13 that displays an image taken from inside of the body of the patient (O) as captured by the endoscope 9 mounted on the arm 6d. As depicted by way of example in FIG. 2, the operation input unit 14 includes two handles, namely, left handle 15 and right handle and 16, to be held by both hands of the operator, and a selector switch 17. One or two of the four arms 6a, 6b, 6c, and 6d, for example, the second arm 6b and third arm 6c can be selected by the selector switch 17. The selected respective second and third arms 6b and 6c is operated by controlling the two handles 15 and 16. The respective second and third arms 6b and 6c selected by the selector switch 17 are defined as operation targets, while the respective one and fourth arms 6a and 6d which have not been selected are defined as operation non-targets.

The medical system 1 is configured so that the operator can direct the arms 6b and 6c and surgical instruments 10 to treat an affected part of the patient (O) by controlling the operation input unit 14 while observing an image of the affected part and the free end portions of the surgical instruments 10 as displayed on the monitor 13.

The controller 5 includes the position and orientation computing unit 18 and an interference prediction unit 19. The position and orientation computing unit 18 computes the target angles, or operation target positions, of the individual joints of the respective arms 6a and 6c as operation targets based on the operation commands inputted by controlling the handles of the operation input unit 14. The interference prediction unit 19 predicts any interference with respect to the arms 6a and 6d as operation non-targets based on the target angles of the individual joints as computed by the position and orientation computing unit 18. The controller 5 also includes a preferential drive setting unit 22, or degree-of-priority calculating unit, and a drive command generation unit 20. The preferential drive setting unit 22, or degree-of-priority calculating unit, calculates the degrees of priority of the respective arms 6a, 6b, 6c and 6d based on the attributes of the first and second medical devices 9 and 10 as detected by the attribute sensors 21 and the results of the prediction by the interference prediction unit 19. The preferential drive setting unit 22, or degree-of-priority calculating unit, outputs information of the arm having the highest degree of priority. The drive command generation unit 20 operates the arm 6a, 6b, 6c or 6d, the degree of priority of which is the highest, based on the information outputted from the preferential drive setting unit 22. The position and orientation computing unit 18 is configured to compute the target angles of the individual joints required to achieve the positions and orientations of the surgical instruments 10 according to the operation commands inputted through the operation input unit 14 by the 6-axes joint groups 8b and 8c of the arms 6b and 6c as operation targets other than the joints having redundant degrees of freedom. The 6-axes joint groups mean there are six degrees of freedom. Consequently, the angles of the individual joints of the arms 6b and 6c, which correspond to the operation commands, are decidedly determined so that the target angles are computed with reduced computational complexity.

On the other hand, the interference prediction unit 19 is configured to predict the existence or non-existence of any interference between two of the mechanical sections (not depicted) of the arms 6a, 6b, 6c and 6d based on the target angles of the individual joints of the arms 6b and 6c as operation targets that computed by the position and orientation computing unit 18 and the current angles of the individual joints of the arms 6a and 6d as operation non-targets. Since the dimensions or the like of the mechanical sections are known in advance, the existence or non-existence of any interference between two of the mechanical sections of the arms 6a, 6b, 6c and 6d is easily predicted.

The medical system 1 is configured such that if the existence of any interference is predicted by the interference prediction unit 19, the degrees of priority of the respective arms 6a, 6b, 6c and 6d are calculated at the preferential drive setting unit 22 based on the attributes of the first and second medical devices 9 and 10 as outputted from the attribute sensors 21. Then the drive command generation unit 20 outputs a drive command signal to make the arm 6a, 6b, 6c or 6d perform an interference avoidance maneuver on which the respective first or second medical device 9 or 10 having the highest degree of priority is mounted. The degree of priority of each arm is calculated, for example, by summing the scores assigned to the attributes of the associated first or second medical device 9 or 10.

With respect to the arms 6b and 6c as operation targets, the drive command generation unit 20 generates drive command signals for driving the individual joints and sends them to the drive units 11 based on the target angles of the individual joints computed at the position and orientation computing unit 18. Each of the arms 6a and 6d are set to preferentially perform an interference avoidance maneuver by the preferential drive setting unit 22. On the other hand, the drive command generation unit 20 generates drive command signals for the individual joints so that by operating the joint groups 8a and 8d including the joints that provide the redundant degree of freedom, the arms 6a and 6d are moved in directions away from the other arms 6b and 6c while maintaining the positions and orientations of the surgical instrument 10 and endoscope 9 mounted thereon. In short, if an interference is predicted and the arms that set to preferentially perform an interference avoidance maneuver are the arms 6a and 6d as operation non-targets, then the drive command generation unit 20 generates drive command signals to allow the arms 6a and 6d to perform only the interference avoidance maneuver. If the arms that set to preferentially perform an interference avoidance maneuver are the arms 6b and 6c as operation targets, then, the drive command generation unit 20 generates drive command signals formed by combining drive command signals, which in turn drive the individual joints based on the target angles for the individual joints, with drive command signals that allow to perform the interference avoidance maneuver.

In the method of operation of the medical system 1 according to this embodiment, as illustrated in FIG. 3, one or two arms 6b and 6c are set as an operation target or operation targets by the selector switch 17 of the operation input unit 14 in step S1, and a determination is then made as to whether an operation command has been inputted by the left handle 15 or right handle 16 of the operation input unit 14 in step S2. If the operation command has been inputted, the target angles of the individual joints that form the arms 6b and 6c set as operation targets corresponding to the handle 15 or 16 by which the operation command has been inputted are calculated in step S3. Here, with respect to the arms 6b and 6c as operation targets, the target angles of a least number of joints that can achieve the position and attitude of the medical device 10 corresponding to the operation command inputted from the handle 15 or 16 are calculated.

Subsequent to the calculation of the target angles of the individual joints of the arms 6b and 6c as an operation target, predictive computation of the existence or non-existence of any interference with the arms 6a, and 6d as operation non-targets is performed prediction in step S4. The result of the prediction in the prediction step S4 is determined step S5. If an interference is predicted, the degrees of priority of the arms 6a, 6b, 6c and 6d are calculated in degree-of-priority calculating step S6, and the arm 6a, 6b, 6c or 6d of the degree of priority of which is the highest is set as an arm that will perform an interference avoidance maneuver in degree-of-priority calculating step S7. In the degree-of-priority calculating step S6, the degrees of priority of the arms 6a, 6b, 6c and 6d are calculated according to the attributes of the associated respective first and second medical devices 9 and 10 as detected by the attribute sensors 21 mounted on the free ends of the arms 6a, 6b, 6c and 6d.

If the attributes of the respective first and second medical devices 9 and 10 are the types of the medical devices 9 and 10, then calculations are performed so that the degree of priority of the arm 6a in which the endoscope 9 is mounted becomes high. The degree of priority of the arm 6a in which grasping forceps or surgical instrument 10 is mounted becomes lower than that of the arm 6a, then the degree of priority of the arm in which an energy device like the high-frequency device or surgical instrument 10 is mounted becomes lowest. If the attributes of the respective first and second medical devices 9 and 10 are in their operation states, calculations are performed so that the degree of priority of each arm becomes low if the respective medical device is in operation, for example, if the grasping forceps 10 are holding or the high-frequency device 10 is energized. Further, if the attributes of the respective first and second medical devices 9 and 10 are external forces, calculations are performed so that the smaller the external force applied to the free end portion of the respective first and second medical device 9 or 10, the higher the degree of priority of the associated arm.

Drive command signals for the individual joints of each arm 6a, 6b, 6c or 6d, which has been set as an arm that is to perform an interference avoidance maneuver, and the arms 6b and 6c as operation targets are then generated at the drive command generation unit 20 in step S8. If the arm 6a or 6d as an operation non-target is set as an arm that is to perform an interference avoidance maneuver, the drive command generation unit 20 generates a drive command signal to operate the joint group 8a or 8d, which has the redundant degree of freedom, so that only the positions of one or more joints on a base end side are moved while maintaining the position and orientation of the respective first and second medical device 9 or 10 mounted on the free end of the arm. If the arm 6b or 6c as an operation target is set as an arm that is to perform an interference avoidance maneuver then, the drive command generation unit 20 generates drive command signals formed by combining drive command signals for achieving the computed target angle with drive command signals that operate the joint group 8b or 8c. Therefore, the drive command signals that operate the joint group 8b or 8c has the redundant degree of freedom, so that one or more joints on the base end side are moved while maintaining the position and orientation of the surgical instrument 10 mounted on the free end of the arm in step S9.

If no interference is predicted as a result of the prediction by the prediction step S4, then processing is performed from step S8 onwards, and only for the arm 6b and 6c as an operation target, a drive command signal is generated for achieving the computed target angle. Based on the drive command signal that generated, the corresponding drive unit 11 is driven in step S9.

As has been described above, according to the medical system 1 of this embodiment and the method of operation thereof, if an interference is predicted, then the interference is avoided by operating the arm having the highest degree of priority. specifically, the arm with the highest degree of priority can be one or more of the arm 6a, 6b, 6c or 6d provided with the first and second medical device 9 or 10, which has a smallest effect on the patient in a direction apart from the remaining arms so as to bringing about an advantage that the remaining arms, each of which has a greater effect on the patient, are not required to perform an interference avoidance maneuver. In other words, the remaining arms, each of which has the greater effect on the patient, are each required to accurately operate responsive to an operation command inputted by the left handle 15 or right handle 16 of the operation input unit 14. If an interference avoidance maneuver is combined, then, the computational complexity becomes huge, and therefore lowering of the accuracy of the maneuver is resulted. Concerning the arm having the smallest effect on the patient (O), the load on the patient would be small and poses no problem even if the computational complexity becomes huge and the accuracy of the maneuver is lowered.

Accordingly, there is a merit that owing to the reduction of the load of computation, interferences of the arms 6a, 6b, 6c and 6d can be avoided more definitely while reducing the load on the patient (O). In this embodiment, the respective first and second medical devices 9 and 10 and the operation states thereof, and the magnitudes of external forces applied to the free end portions of the respective first and second medical devices 9 and 10 are exemplified as the attributes of the respective first and second medical devices 9 and 10 for the calculation of the degrees of priority of the associated arms. These three types of attributes may all be used as indexes, or one of two of them may be used as indexes.

The degrees of priority of the arms may be set beforehand based on the attributes of the medical devices mounted thereon, for example, in an ascending order like the high-frequency of second medical device 10 under energization, the medical device 10 with a large external force applied to the free end portion thereof, the high-frequency device 10 under no energization, and the endoscope 9 with a small external force applied to the free end portion thereof.

In this embodiment, the medical system 1 has been described by way of example with the four arms 6a, 6b, 6c, and 6d. However, the medical system 1 may be provided with a desired number of arms insofar as the number of the arms is two or more. Further, the degrees of freedom of the respective arms 6a, 6b, 6c, and 6d may be with a desired number of axes insofar as the number of the axes is seven or more.

In this embodiment, it is configured to perform an interference avoidance maneuver by only the arm 6a, 6b, 6c or 6d having the highest degree of freedom. However, it may also be configured to perform an interference avoidance maneuver by each of the plurality of one of the arms 6a, 6b, 6c, and 6d, the plurality of arms can be selected in a descending order of the degree of priority. If an interference cannot be avoided by only the arm 6a, 6b, 6c or 6d having the highest degree of priority, it may also be configured to restrict or stop the maneuver of the arm 6b and/or the arm 6c as operation targets or an operation target.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A medical system comprising:
a plurality of arms each of which comprising a joint group having a redundant degree of freedom and wherein the plurality of arms being configured to move one or more medical devices mounted on a free end thereof;
an operation portion configured to input an operation command for operating at least one of the plurality of arms; and
a controller configured to control the at least one of the plurality of arms based on the operation command from the operation portion, the controller comprises one or more processor as a hardware,
wherein the one or more processors configured to:
predict an interference between the plurality of arms;
calculate degrees of priority of each of the plurality of arms based on severities of effects by the predicted interference on a patient; and
generate a signal of one of the plurality of arms having highest one of the degrees of priority, the signal is configured that the one of the plurality of arms can avoid the interference.

2. The medical system of claim 1, wherein the one or more processors are configured to calculate the degrees of priority based on types of the medical devices being mounted on the arms.

3. The medical system of claim 1, wherein the one or more processors are configured to calculate the degrees of priority based on operation states of the medical devices being mounted on the arms.

4. The medical system of claim 1 further comprises external force detection sensors that detect external forces applied to the medical devices, and
wherein the one or more processors are configured to calculate the degrees of priority in proportion to magnitudes of the external forces detected by the external force detection sensors.

5. The medical system of claim 1, wherein the signal is for redundant degrees of freedom of the one of the plurality of arms.

6. A method of operation for a medical system, the method comprising:
predicting an interference between plurality of arms,
calculating degrees of priority of each of the plurality of arms based on severities of effects by the predicted interference on a patient, and
generating a signal of one of the plurality of arms having highest one of the degrees of priority, the signal is configured that the one of the plurality of arms can avoid the interference.

* * * * *